United States Patent [19]
Nilsen et al.

[11] Patent Number: 6,013,447
[45] Date of Patent: Jan. 11, 2000

[54] RANDOM INTRACELLULAR METHOD FOR OBTAINING OPTIMALLY ACTIVE NUCLEIC ACID MOLECULES

[75] Inventors: Timothy W. Nilsen, Russell, Ohio; Hugh D. Robertson, New York, N.Y.; Thomas J. Kindt, Bethesda, Md.

[73] Assignee: Innovir Laboratories, Inc., Wilmington, Del.

[21] Appl. No.: 08/976,220

[22] Filed: Nov. 21, 1997

[51] Int. Cl.[7] .............................. C12Q 1/68; C07H 21/04; C07H 21/02; C12N 15/63

[52] U.S. Cl. ........................ 435/6; 435/69.1; 435/91.31; 435/320.1; 435/455; 536/23.1; 536/23.4; 536/24.1; 536/24.5

[58] Field of Search .............................. 435/6, 69.1, 91.1, 435/91.31, 172.1, 45, 320.1; 536/23.1, 23.4, 24.1, 24.5; 514/44

[56] References Cited

U.S. PATENT DOCUMENTS

| | | |
|---|---|---|
| 4,987,071 | 1/1991 | Cech et al. . |
| 5,168,053 | 12/1992 | Atlman et al. . |
| 5,225,347 | 7/1993 | Robertson . |
| 5,254,678 | 10/1993 | Haseloff et al. . |
| 5,334,711 | 8/1994 | Sproat et al. . |
| 5,422,251 | 6/1995 | Fresco . |
| 5,496,698 | 3/1996 | Draper et al. ................................ 435/6 |
| 5,525,468 | 6/1996 | McSwiggen . |
| 5,527,895 | 6/1996 | Hampel et al. . |
| 5,580,967 | 12/1996 | Joyce . |
| 5,624,824 | 4/1997 | Yuan et al. . |

FOREIGN PATENT DOCUMENTS

| | | |
|---|---|---|
| 0 321 021 | 6/1989 | European Pat. Off. . |
| WO 88/04300 | 6/1988 | WIPO . |
| WO 89/05852 | 6/1989 | WIPO . |
| WO 91/04319 | 4/1991 | WIPO . |
| WO 91/04324 | 4/1991 | WIPO . |
| WO 92/03566 | 3/1992 | WIPO . |
| WO 93/22434 | 11/1993 | WIPO . |
| WO 94/13791 | 6/1994 | WIPO . |
| WO 95/23225 | 8/1995 | WIPO . |
| WO 95/24489 | 9/1995 | WIPO . |
| WO 96/18733 | 6/1996 | WIPO . |
| WO 96/21731 | 7/1996 | WIPO . |
| Wo 97/10360 | 3/1997 | WIPO . |
| WO 97/18312 | 5/1997 | WIPO . |
| WO 97/33991 | 9/1997 | WIPO . |

OTHER PUBLICATIONS

Kawasaki et al. "Selection of the Best Target Site for Ribozyme–Mediated Cleavage within a Fusion Gene for Adenovirus E1A–Associated 300 kDa Protein (p300) and Luciferase" Nucleic Acids Research vol. 24(15): 3010–3016, 1996.

Lima et al. "Combinatorial Screening and Rational Optimization for Hybridization to Folded Hepatitis C Virus RNA of Oligonucleotides with Biological Antisense Activity" The Journal Of Biological Chemistry vol. 272(1): 626–638, Jan. 3, 1997.

Altman, "RNA Enzyme–Directed Gene Therapy," *Proc. Natl. Acad. Sci. USA* 90:10898–10900 (1993).

Baer, et al., "Structure And Transcription Of A Human Gene Fro(?) H1 RNA, The RNA Component Of Human RNase P," *Nucleic Acids Research* 18:97–103 (1989).

Beal, et al., "The Influence of Single Base Triplet Changes on the Stability of a Pur·Pur·Pyr Triple Helix Determined by Affinity Cleaving," *Nuc. Acids Res.* 20(11):2773–2776 (1992).

Beal, et al., "Second Structural Motif for Recognition of DNA by Oligonucleotide–Directed Triple–Helix Formation," *Science* 251:1360–1363 (1991).

Blume, et al., "Triple Helix Formation by Purine–Rich Oligonucleotides Targeted to the Human Dihydrofolate Reductase Promoter," *Nucleic Acids Res.* 20:1777–1784 (1992).

Buzayan et al., *Proc. Natl. Acad. Sci. USA* 83:8859–8862 (1968).

Cech, "Self–Splicing Of Group I Introns," *Annu. Rev. Biochem.* 59:543–568 (1990).

Chalfie, et al., "Green Fluorescent Protein as a Marker for Gene Expressions" *Science* 263:802–805 (1994).

Cooney, et al., "Site–Specific Oligonucleotide Binding Represses Transcription of the Human c–myc Gene in Vitro," *Science* 241:456–459 (1988).

(List continued on next page.)

*Primary Examiner*—Nancy Degen
*Assistant Examiner*—Sean McGarry
*Attorney, Agent, or Firm*—Arnall Golden & Gregory, LLP

[57] ABSTRACT

Vectors and a method for the identification of affector RNA molecules, such as ribozymes, external guide sequences, anti-sense RNA, and triple helix-forming RNA, that inhibit expression of target RNA molecules are disclosed. The method identifies functional affector RNA molecules by screening or selecting for those RNA molecules that inhibit expression of a fusion transcript, which includes the sequence of an RNA molecule of interest, from a library of potential affector RNA molecules. The vectors include a reporter gene encoding the fusion transcript including the RNA molecule of interest and RNA encoding the reporter protein. The vectors also include a second reporter gene encoding a second reporter protein. Expression of the second reporter protein can be used both to detect transformation or transfection of the vector into cells and as a control for effects on the expression of the first reporter protein that are not due to inhibition of expression of the RNA molecule of interest. The vector also encodes an affector RNA molecule targeted to the RNA of interest. A key advantage of the disclosed method and vectors is the assessment of inhibition of expression of an RNA of interest in an in vivo setting which will be the same or similar to the setting where identified affector molecules will be used. Another advantage of the disclosed method is that all, or a substantial number of the accessible sites in the RNA of interest can be determined in one assay. Also disclosed are affector oligomers based on affector RNA molecules identified as inhibiting the expression of an RNA of interest. The disclosed method also allows direct comparison of the inhibitory activities of different affector RNA molecules directed to different target sites.

34 Claims, 3 Drawing Sheets

OTHER PUBLICATIONS

Cormack, et al., "FACS–optimized Mutants of the Green Fluorescent Protein (GFP)," *Gene* 173:33–38 (1996).

Durland, et al., "Binding of Triple Helix Forming Oligonucleotides to Sites in Gene Promoters," *Biochemistry* 30:9246–9255 (1991).

Duval–Valentin, et al., "Specific Inhibition of Transcription by Triple Helix–Forming Oligonucleotides," *Proc. Natl. Acad. Sci. USA* 89:504–508 (1992).

Forster, et al., "External Guide Sequences For An RNA Enzyme," *Science* 249:783–786 (1990).

Forster, et al., "Self–Cleavage Of Virusoid RNA Is Performed By The Proposed 55–Nucleotide Active Site," *Cell* 50:9–16 (1987).

Fowlkes, et al., "Transcriptional Control Regions Of The Adenovirus VAI RNA Gene," *Cell* 22:405–413 (1980).

Francois, et al., "Sequence–Specific Recognition and Cleavage of Duplex DNA via Triple–Helix Formation by Oligonucleotides Covalently Linked to a Phenanthroline–Copper Chelate," *Proc. Natl. Acad. Sci. USA* 86:9702–9706 (1989).

Graham, et al., "Characteristics of a Human Cell Line Transformed by DNA from Human Adenovirus Type 5," *J. Gen Virol.* 36:59–72 (1977).

Grigoriev, et al., "A Triple Helix–Forming Oligonucleotide–Intercalator Conjugate Acts As A Transcriptional Repressor Via Inhibition Of NF κB Binding To Interleukin–2 Receptor," *J. Biol. Chem.* 267:3389–3395 (1992).

Guerrier–takada, et al., "The RNA Moiety Of Ribonuclease P Is The Catalytic Subunit Of The Enzyme," *Cell* 35:849–857 (1983).

Gupta, et al., "Compliation Of Small RNA Sequences," *Nucleic Acids Res.* 19:2073–2075 (1990).

Hall, et al., "Transcription Initiation Of Eucaryotic Transfer RNA Genes," *Cell* 29:3–5 (1982).

Hannon, et al., "Multiple cis–Acting Elements Are Required for RNA Polymerase III Transcription of the Gene Encoding H1 RNA, the RNA Component of Human RNase P," *J. Biol. Chem.* 266:22796–22799 (1991).

Haseloff and Gerlach, "Simple RNA Enzymes with New and Highly Specific Endoribonuclease Activities," *Nature* 334:585–591 (1988).

Kickoefer, et al., "Vault Ribonucleoprotein Particles From Rat And Bullfrog Contain A Related Small RNA That Is Transcribed By RNA Polymerase III," *J. Biol. Chem.* 268:7868–7873 (1993).

Kunkel, et al., "U6 Small Nuclear RNA Is Transcribed By RNA Polymerase III," *Proc. Natl. Acad. Sci. USA* 83:8575–8579 (1987).

Kunkel, et al., "Transcription Of A Human U6 Small Nuclear RNA Gene In Vivo Withstands Deletion Of Intragenic Sequences But Not Of An Upstream TATATA Box," *Nucleic Acids Res.* 18:7371–7379 (1989).

Lieber and Strauss, "Selection of Efficient Cleavage Sites in Target RNAs by Using a Ribozyme Expression Library," *Mol. Cell. Biol.* 8:466–472 (1995).

Lin, et al., "Use of EDTA Derivatization To Characterize Interactions Between Oligodeoxyribonucleoside Methylphosphonates and Nucleic Acids," *Biochemistry* 28:1054–1061 (1989).

Liu and Altman, "Inhibition of Viral Gene Expression by the Catalytic RNA Subunit of RNase P from *Escherichia coli*," *Genes Dev.* 9:471–480 (1995).

Lomant and Fresco, "Structural and Energetic Consequences of Noncomplementary Base Oppositions in Nucleic Acid Helices" *Prog. Nucl. Acid Res. Mol. Biol.* 15:185 (1975).

Maher, et al., "Inhibition Of DNA Binding Proteins By Oligonucleotide–Directed Triple Helix Formation," *Science* 245:725–730 (1989).

Maher, et al., "Analysis of Promoter–Specific Repression by Triple–Helical DNA Complexes in a Eukaryotic Cell–Free Transcription System," *Biochemistry* 31:70–81 (1992).

Mather, "Establishment and Characterization of Two Distinct Mouse Testicular Epithelial Cell Lines," *Biol. Reprod.* 23:243–252 (1980).

Mather, et al., "Culture of Testicular Cells in Hormone–Supplemented Serum–Free Medium," *Annals N. Y. Acad. Sci* 383:44–68 (1982).

Mergny, et al., "Sequence Specificity in Triple–Helix Formation: Experimental and Theoretical Studies of the Effect of Mismatches on Triplex Stability," *Biochemistry* 30:9791–9798 (1991).

Moser and Dervan, "Sequence–Specific Cleavage of Double Helical DNA by Triple Helix Formation," *Science* 238:645–650 (1987).

Mosinger, et al., "Cloning and Characterization of a Mouse cDNA Encoding a Cytoplasmic Protein–Tryrosine–Phosphatase," *Proc. Natl. Acad. Sci. USA* 89:499–503 (1992).

Nielsen, et al., "Transcription Of Human 5S rRNA Genes Is Influenced By An Upstream DNA Sequence," *Nucleic Acids Res.* 21:3631–3636 (1993).

Noonberg, et al., "In Vivo Generation Of Highly Abundant Sequence–Specific Oligonucleotide For Antisense And Triplex Gene Regulation," *Nucleic Acids Res.*, 22:2830–2836 (1995).

Offensperger, et al. "In vivo inhibition of duck hepatitis B virus replication and gene expressions by phosphorothioate modified antisense oligodeoxynucleotides," *The EMBO Journal* 12(3): 1257–1262 (1993).

Orson, et al., "Oligonucleotide Inhibition Of IL2Rα mRNA Transcription by Promoter Region Collinear Triplex Formation In Lymphocytes," *Nucleic Acids Res.* 19:34535–3441 (1991).

Pei, et al., "Site–Specific Cleavage of Duplex DNA by a Semisynthetic Nuclease via Triple–Helix Formation," *Proc. Natl. Acad. Sci. USA* 87:9858–9862 (1990).

Perrouault, et al., "Sequence–Specific Artificial Photo–Induced Endonucleases Based on Triple Helix–Forming Oligonucleotides," *Nature* 344:358–360 (1990).

Postel, et al., "Evidence that a Triple–Forming Oligodeoxyribonucleotide Binds to the c–myc Promoter in HeLa Cells, Thereby Reducing c–myc mRNA Levels," *Proc. Natl. Acad. Sci. USA* 88:8227–8231 (1991).

Posvic and Dervan, "Sequence–Specific Alkylation of Double–Helical DNA by Oligonucleotide–Directed Triple–Helix Formation," *J. Am. Chem Soc.* 112:9428–9430 (1992).

Praseuth, et al., "Sequence–Specific Binding and Photo-crosslinking of a α and β Oligodeoxynucleotides to the Major Groove of DNA via Triple–Helix Formation," *Proc. Natl. Acad. Sci. USA* 85:1349–1353 (1988).

Reddy, et al., "The Capped U6 Small Nuclear RNA Is Transcribed By RNA Polymerase III," *J. Biol. Chem.* 262:75–81 (1987).

Romero, et al, "A Conserved Secondary Structure For Telomerase RNA," *Cell* 67:343–353 (1991).

Rossi, et al., "Exploring The Use Of Antisense, Enzymatic RNA Molecules (Ribozymes) As Therapeutic Agents," *Antisense Res. Dev.* 1:285–288 (1991).

Ruffner, et al., "Sequence Requirements of the Hammerhead RNA Self–Cleavage Reaction," *Biochemistry* 29:10695–10702 (1990).

Shimayama, et al., "Generality of the NUX Rule: Kinetic Analysis of the Results of Systematic Mutations in the Trinucleotide at the Cleavage Site of Hammerhead Ribozymes," *Biochemistry* 34:3649–3654 (1995).

Strobel, et al., "Site–Specific Cleavage of Human Chromosome 4 Mediated by Triple–Helix Formation," *Science* 254:1639–1642 (1991).

Symons, "Small Catalytic RNAs," *Annu. Rev. Biochem.* 61:641–671 (1992).

Takasugi, et al., "Sequence–Specific Photo–Induced Cross–Linking of the Two Strands of Double–Helical DNA by a Psoralen Covalently Linked to a Triple Helix–Forming Oligonucleotide," *Proc. Natl. Acad. Sci. USA* 88:5602–5606 (1991).

Topal and Fresco, "Complementary Base Pairing and the Origin of Substitution Mutations," *Nature* 263:285–289 (1976).

Urlaub and Chasin, "Isolation of Chines hamster cell mutants deficient in dihydrofolate reductase activity" *Proc. Natl. Acad. Sci. USA* 77:4216 (1980).

Young, et al., "Triple Helix Formation Inhibits Transcription Elongation in vitro," *Proc. Natl. Acad. Sci. USA* 88:10023–10026 (1991).

Yuan, et al., "Targeted Cleavage Of mRNA By Human RNase P," *Proc. Natl. Acad. Sci. USA* 89:8006–8010 (1992).

Zhuang and Weiner, "A Compensatory Base Change in U1 snRNA Suppresses a 5' Splice Site Mutation," *Cell* 46:827–835 (1986).

Zolotukhin, et al., "A 'Humanized' Green Fluorescent Protein cDNA Adapted for High–Level Expression in Mammalian Cells," *J. Virol* 70:4646–4654 (1996).

Zoumadakis and Tabler, "Comparative Analysis of Cleavage Rates After Systematic Permutation of the NUX↓ Consensus Target Motif for Hammerhead Ribozymes," *Nucl. Acids Res.* 23:1192–1196 (1995).

Guerrier–Takada, et al., "Artificial regulation of gene expression in Escherichia coli by RNase P" *Proc. Natl. Acad. Sci. U.S.A.* 92:11115–11119 (1995).

Guerrier–Takeda, et al. "Phenotypic conversion of drug–resistant bacteria to drug sensitivity," *Proc. Natl. Acad. USA* 94:8468–8472 (1997).

Yuan & Altman, "Selection of guide sequences that dirct efficient cleavage of mRNA by Human Ribonuclease P," *Science* 263:1269–1273 (1994).

RANDOM INTRACELLULAR METHOD FOR OBTAINING OPTIMALLY ACTIVE NUCLEIC ACID MOLECULES

BACKGROUND OF THE INVENTION

This is generally in the field of biologically active nucleic acid molecules, such as external guide sequences, ribozymes, antisense RNA, and triple helix-forming RNA, and specifically in the area of methods for the identification of sites in target RNA that are accessible to such biologically nucleic acid molecules.

Ribonucleic acid (RNA) molecules can serve not only as carriers of genetic information, for example, genomic retroviral RNA and messenger RNA (mRNA) molecules and as structures essential for protein synthesis, for example, transfer RNA (tRNA) and ribosomal RNA (rRNA) molecules, but also as enzymes which specifically cleave nucleic acid molecules. Such catalytic RNA molecules are called ribozymes.

Drs. Altman and Cech were awarded the Nobel prize in 1989 for the discovery of catalytic RNA. This discovery has generated much interest in commercial applications of ribozymes, particularly in therapeutics (Altman, *Proc. Natl. Acad. Sci. USA* 90:10898–10900 (1993); Symons, *Annu. Rev. Biochem.* 61:641–671 (1992); Rossi et al., *Antisense Res. Dev.*, 1:285–288 (1991); Cech, *Annu. Rev. Biochem.* 59:543–568, (1990)). Several classes of catalytic RNAs (ribozymes) have been described, including intron-derived ribozymes (WO 88/04300; see also, Cech, *Annu. Rev. Biochem.*, 59:543–568, (1990)), hammerhead ribozymes (WO 89/05852 and EP 321021 by GeneShears), hairpin ribozymes (U.S. Pat. No. 5,527,895 to Hampel et al.), and axehead ribozymes (WO 91/04319 and WO 91/04324 by Innovir). Analogues of hammerhead ribozymes useful for specific cleavage of RNA molecules are described in U.S. Pat. No. 5,334,711. Oligomers based on hammerhead ribozymes in which the oligomer and the target RNA each contribute part of the catalytic core are described in WO 97/18312.

Another class of ribozymes includes the RNA portion of an enzyme, RNAse P, which is involved in the processing of transfer RNA (tRNA), a common cellular component of the protein synthesis machinery. Bacterial RNAse P includes two components, a protein (C5) and an RNA (M1). Sidney Altman and his coworkers demonstrated that the M1 RNA is capable of functioning just like the complete enzyme, showing that in *Escherichia coli* the RNA is essentially the catalytic component, (Guerrier-Takada et al., *Cell* 35:849–857 (1983)). In subsequent work, Dr. Altman and colleagues developed a method for converting virtually any RNA sequence into a substrate for bacterial RNAse P by using an external guide sequence (EGS), having at its 5' terminus at least seven nucleotides complementary to the nucleotides 3' to the cleavage site in the RNA to be cleaved and at its 5' terminus the nucleotides NCCA (N is any nucleotide)(WO 92/03566 by Yale University, U.S. Pat. No. 5,168,053, and Forster and Altman, *Science* 238:407–409 (1990)). Using similar principles, EGS/RNAse P-directed cleavage of RNA has been developed for use in eukaryotic systems, (Yuan et al., *Proc. Natl. Acad. Sci. USA* 89:8006–8010 (1992); U.S. Pat. No. 5,624,824; WO 95/24489 by Yale University). A short form of eukaryotic external guide sequence has also been described (WO 97/33991 by Innovir Laboratories, Inc.). As used herein, "external guide sequence" and "EGS" refer to any oligonucleotide that forms an active cleavage site for RNAse P in a target RNA.

Although ribozymes theoretically can cleave any desired site in an RNA molecule, in reality not all sites are efficiently cleaved by ribozymes designed or targeted to cleave them. This is especially true in vivo where numerous examples have been described of sites that are inefficiently cleaved by targeted ribozymes. The problem is not a total lack of sites in an RNA molecule of interest, but rather determining which sites, among the many possible sites, can be cleaved most efficiently. This is important since it is often desirable to identify the most efficient sites of cleavage and not just any site that can be cleaved. The process of targeting one or a few sites on an RNA molecule essentially at random and then testing for cleavage is not likely to identify the most efficient sites. Comprehensive testing of all sites is not practical because of the amount of labor involved in making and testing each ribozyme or external guide sequence. WO 96/21731 by Innovir describes selection of efficiently cleaved sites in this manner by making and testing 80 different external guide sequences targeted to different sites. However, this represented only a fraction of the possible sites. Techniques for identifying sites that accessible for cleavage are described in U.S. Pat. No. 5,525,468 and U.S. Pat. No. 5,496,698.

Kawasaki et al., *Nucl. Acids Res.* 24(15):3010–3016 (1996), describes the use of a transcript encoding a fusion between adenovirus E1A-associated 300 kDa protein (p300) and luciferase to assess the efficiency with which sites in the p300 RNA are cleaved by hammerhead ribozymes in vivo. A few hammerhead ribozymes targeted to sites having GUX triplets (which are required for cleavage by a hammerhead ribozyme) were designed and expressed from a vector in cells. A separate vector expressed the p300-luciferase fusion RNA. Cleavage of sites in the p300 portion of the transcript was assessed by measuring luciferase activity. Kawasaki et al. tested each ribozyme separately.

As an alternative to testing for cleavable sites, or preliminary to such testing, attempts have also been made to predict which sites will be accessible from theoretical considerations or by empirically testing the presence or absence of secondary or tertiary structure at sites in RNA molecules. For example, Ruffner et al., *Biochemistry* 29:10695–10702 (1990), Zoumadakis and Tabler, *Nucl. Acids Res.* 23:1192–1196 (1995), Shimayama et al., *Biochemistry* 34:3649–3654 (1995), Haseloff and Gerlach, *Nature* 334:585–591 (1988), and Lieber and Strauss, *Mol. Cell. Biol.* 8:466–472 (1995), describe attempts to use rules of structure formation in RNA to predict cleavable sites. However, the structure of RNA molecules cannot be accurately predicted from theoretical considerations and the determination of actual secondary and tertiary structure of an RNA molecule requires extensive experimentation. Such determinations are often of marginal value since structural determinations are carried out in vitro while the in vivo structure may be different. Accordingly, it would be useful to have a method of determining which sites in an RNA molecule can be efficiently cleaved in vivo. For example, it would be useful to have a method of determining which ribozymes or external guide sequences are most efficient at cleaving or mediating cleavage of an RNA molecule in vivo.

It can also be difficult to identify ribozymes and other biologically active molecules that will function inside cells since not all such biologically active molecules that are functional in vitro are functional in cells because they are, for example, improperly localized, sequestered, or bound by intracellular proteins.

Therefore, it is an object of the present invention to provide a method and compositions for identifying biologically active RNA molecules, such as ribozymes, external guide sequences for ribozymes, antisense RNA, and triple helix-forming RNA, that alter expression of a target RNA molecule most efficiently in vivo.

It is a further object of the present invention to provide a method and compositions for identifying sites in a target RNA, or nucleic acid involved in expression of a target RNA, that are most accessible as target sites for alteration of expression in vivo.

It is a further object of the present invention to provide inhibitory oligomers targeted to sites identified as accessible.

SUMMARY OF THE INVENTION

Vectors and a method for the identification of affector RNA molecules, such as ribozymes, external guide sequences, anti-sense RNA, and triple helix-forming RNA, that alter, or preferably inhibit, expression of target RNA molecules are disclosed. In the preferred embodiments, the method identifies functional affector RNA molecules by screening or selecting for those RNA molecules that inhibit expression of a fusion transcript, which includes the sequence of an RNA molecule of interest, from a library of potential affector RNA molecules. Inhibition of expression of the fusion transcript prevents expression of the reporter protein. This allows inhibition of expression to be monitored by detecting expression of the reporter protein, directly or indirectly. Alteration of expression is accomplished by interaction of a nucleic acid molecule involved in the expression of the RNA molecule of interest with an affector RNA molecule. Ribozymes and external guide sequences result in cleavage of the fusion transcript, and antisense RNA and triple helix-forming RNA block expression through hybridization to a nucleic acid molecule involved in the expression of the fusion transcript.

The vectors include a reporter gene encoding the fusion transcript including the RNA molecule of interest and RNA encoding the reporter protein. The vectors also include a second reporter gene encoding a second reporter protein. Expression of the second reporter protein can be used both to detect transformation or transfection of the vector into cells and as a control for effects on the expression of the first reporter protein that are not due to inhibition of expression of the RNA molecule of interest. The vector also encodes an affector RNA molecule targeted to the RNA of interest. The method preferably uses a set of these vectors where each vector in the set encodes a different affector RNA molecule, each targeted to a different site in the RNA of interest. The set of vectors is transformed or transfected into appropriate cells, and the cells are screened or selected for expression of the second reporter protein. These cells are then screened or selected for those cells which do not express the first reporter protein, or express the reporter protein only at a low level. These cells harbor the most efficient affector RNA molecules which then can be identified by characterizing the vectors in the cells.

A key advantage of the disclosed method and vectors is the assessment of inhibition of expression of an RNA of interest in an in vivo setting which will be the same or similar to the setting where identified affector RNA molecules, or affector oligomers based on such identified RNA molecules, will be used. Another advantage of the disclosed method is that all, or a substantial number of the accessible sites in the RNA of interest can be determined in one assay. Such sites, determined to be accessible for one type of affector molecule, may be accessible for other types of affector molecules. In the case of ribozymes and external guide sequences, the disclosed method allows assessment not just of cleavage of the RNA of interest, but also of an ultimate desired phenotype (that is, loss of the phenotype supported by the RNA of interest) as a result of such cleavage.

Also disclosed are affector oligomers based on affector RNA molecules identified as altering the expression of an RNA of interest. The identified affector RNA molecules, or the targeting sequences in the identified affector RNA molecules, can be used to design affector oligomers targeted to the same site shown to be accessible. While the identification method uses affector molecules composed of ribonucleotides, the base sequence of the identified affector RNA molecules can be used in any form of oligomer, such as peptide nucleic acids or oligonucleotides with chemically modified nucleotide residues.

DETAILED DESCRIPTION OF THE INVENTION

Figure 1:
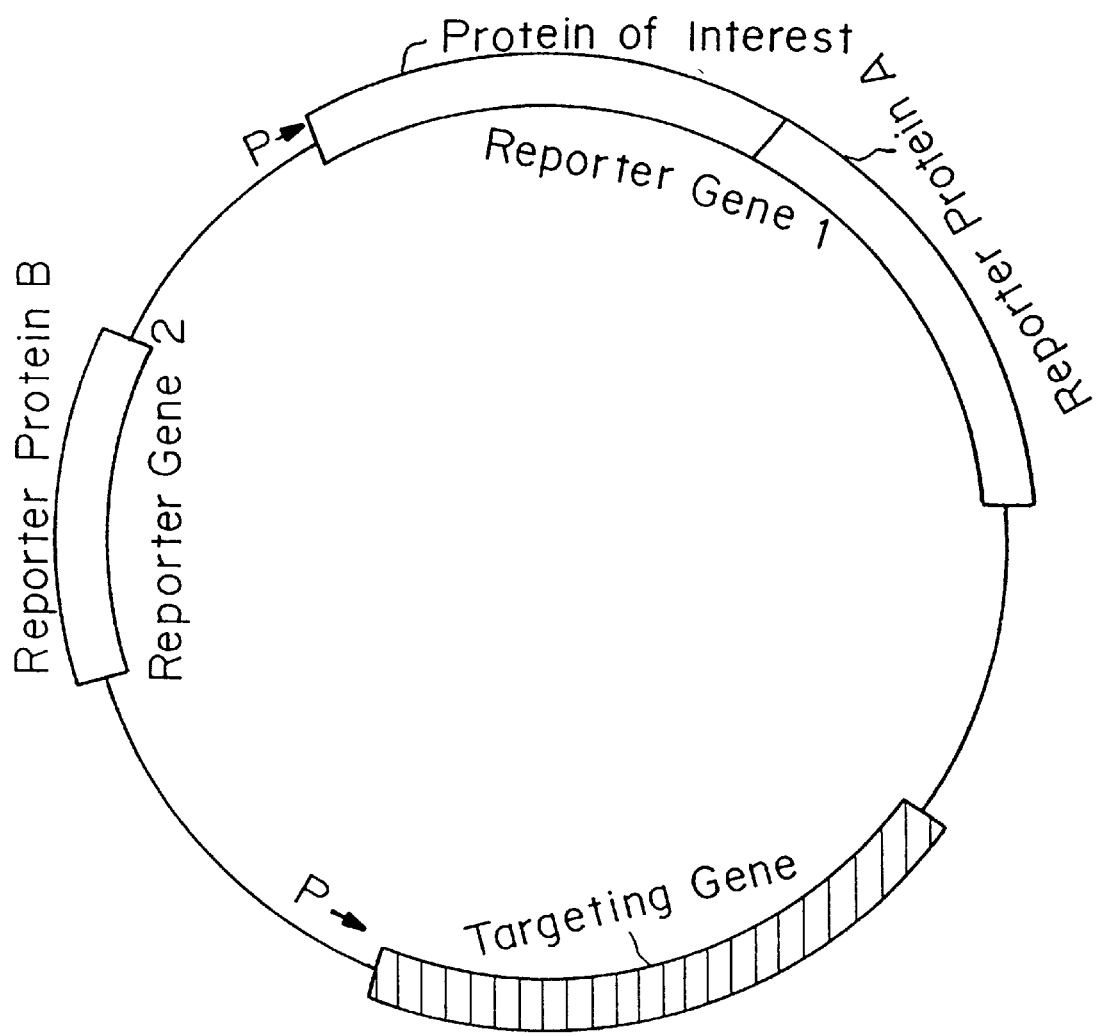
FIG. 1 is a diagram of an example of a vector for use in the disclosed method. Reporter gene 1 encodes a fusion transcript made up of an RNA of interest and RNA encoding a reporter protein (reporter protein A). The fusion transcript encodes a fusion protein made up of the protein encoded by the RNA of interest and reporter protein A. Reporter gene 2 encodes reporter protein B. The targeting gene encodes one of the affector RNA molecules to be tested. The encoded ribozyme is flanked by self-cleaving hammerhead ribozymes which cleave the test ribozyme from the transcript.
Figure 2:
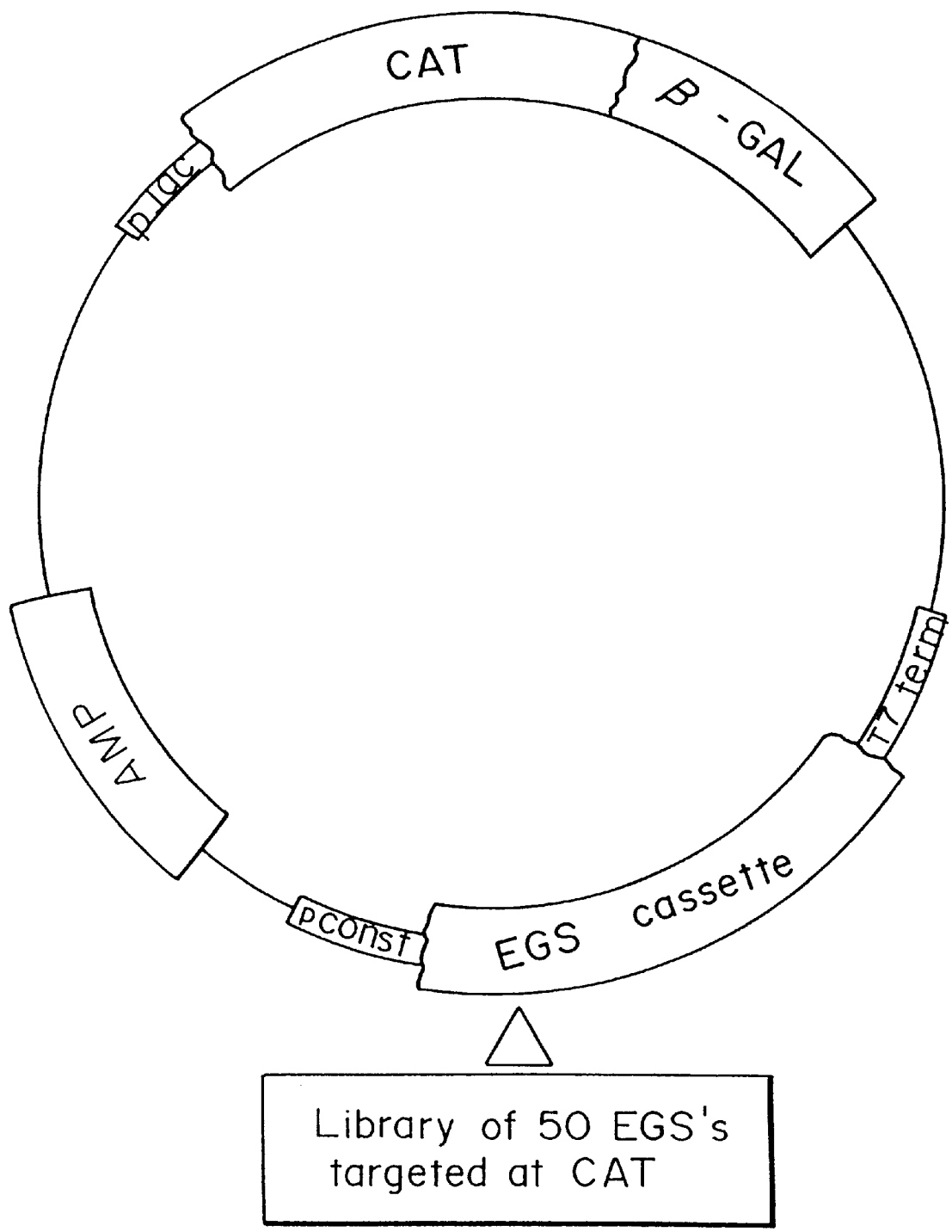
FIG. 2 is a diagram of an example of a vector for use in the disclosed method. Reporter gene 1 encodes a fusion transcript made up of an RNA encoding chloramphenicol acetyltransferase (CAT) and RNA encoding β-galactosidase (reporter protein A). The fusion transcript encodes a fusion protein made up of CAT and β-galactosidase. Reporter gene 2 is an ampicillin resistance gene. The targeting gene is an EGS cassette encoding one of a library of 50 EGS molecules, each targeted to a different site in the CAT RNA.

Vectors and a method for the identification of affector RNA molecules, such as ribozymes, external guide sequences, anti-sense RNA, and triple helix-forming RNA, that inhibit expression of target RNA molecules are disclosed. The method identifies functional affector RNA molecules by screening or selecting for those RNA molecules that alter expression of a fusion transcript, which includes the sequence of an RNA molecule of interest, from a library of potential affector RNA molecules. Inhibition of expression of the fusion transcript prevents expression of the reporter protein. This allows inhibition of expression to be monitored by detecting expression of the reporter protein, directly or indirectly. Alternatively, expression can be increased relative to expression of the molecules relative to expression in cells not including the optimal affector RNA molecule. The inhibition is accomplished by interaction of a nucleic acid molecule involved in the expression of the RNA molecule of interest with an affector RNA molecule. Ribozymes and external guide sequences result in cleavage of the fusion transcript, and antisense RNA and triple helix-forming RNA block expression through hybridization to a nucleic acid molecule involved in the expression of the fusion transcript.

The vectors include a reporter gene encoding the fusion transcript including the RNA molecule of interest and RNA encoding the reporter protein. The vectors also include a second reporter gene encoding a second reporter protein. Expression of the second reporter protein can be used both to detect transformation or transfection of the vector into cells and as a control for effects on the expression of the first reporter protein that are not due to inhibition of expression of the RNA molecule of interest. The vector also encodes an affector RNA molecule targeted to the RNA of interest. The method preferably uses a set of these vectors where each vector in the set encodes a different affector RNA molecule, each targeted to a different site in the RNA of interest. The set of vectors is transformed or transfected into appropriate cells, and the cells are screened or selected for expression of the second reporter protein. These cells are then screened or selected for those cells which do not express the first reporter protein, or express the reporter protein only at a low level. These cells harbor the most efficient affector RNA molecules which then can be identified by characterizing the vectors in the cells.

A key advantage of the disclosed method and vectors is the assessment of alteration of expression of an RNA of interest in an in vivo setting which will be the same or similar to the setting where identified affector RNA molecules, or affector oligomers based on such identified RNA molecules, will be used. Another advantage of the disclosed method is that all, or a substantial number of the accessible sites in the RNA of interest can be determined in one assay. Such sites, determined to be accessible for one type of affector molecule, may be accessible for other types of affector molecules. In the case of ribozymes and external guide sequences, the disclosed method allows assessment not just of cleavage of the RNA of interest, but also of an ultimate desired phenotype (that is, loss of the phenotype supported by the RNA of interest) as a result of such cleavage.

Also disclosed are affector oligomers based on affector RNA molecules identified as altering the expression of an RNA of interest. The identified affector RNA molecules, or the targeting sequences in the identified affector RNA molecules, can be used to design affector oligomers targeted to the same site shown to be accessible. While the identification method uses affector molecules composed of ribonucleotides, the base sequence of the identified affector RNA molecules can be used in any form of oligomer, such as peptide nucleic acids or oligonucleotides with chemically modified nucleotide residues. The disclosed method also allows direct comparison of the inhibitory activities of different affector RNA molecules directed to different target sites.

I. Vectors

The disclosed vectors include a first reporter gene, a second reporter gene, and a targeting gene. The first reporter gene, also referred to herein as reporter gene 1, encodes an RNA molecule including sequence of an RNA molecule of interest and sequence encoding a reporter protein, referred to herein as the first reporter protein or reporter protein A. The second reporter gene encodes another reporter protein, referred to herein as the second reporter protein or reporter protein B, which must be different from the first reporter protein. The vector also encodes an affector RNA molecule either specifically targeted to the RNA of interest or including a degenerate or partially degenerate targeting sequence. Expression, or lack of expression, of the first reporter protein is used to assess the effect of the affector RNA molecule encoded by the targeting gene. Expression of the second reporter protein can be used both to detect transformation or transfection of the vector into cells and as a control for effects on the expression of the first reporter protein that are not due to cleavage of the RNA molecule of interest.

The disclosed vectors are nucleic acid molecules and can be of any suitable form that allows the reporter genes and the targeting gene to be introduced into, and expressed in, appropriate cells. This includes the use of autonomously replicating vectors, viral vectors, nucleic acids that integrate into the host chromosome, and transiently expressed nucleic acid molecules. Although it is preferred that the three components—the first reporter gene, the second reporter gene, and the targeting gene—are included on a single nucleic acid molecule, the reporter genes and the targeting gene may be on separate molecules. When the reporter genes and the targeting gene are on separate molecules, it is preferred that the molecule containing the reporter genes is integrated into the host chromosome. This allows a cell strain containing appropriate reporter genes to be easily maintained and different sets of vectors encoding different libraries of affector RNA molecules to be conveniently tested against the same reporter gene.

It is preferred that plasmid vectors containing promoters and control sequences which are derived from species compatible with the host cell be used with these hosts. It is preferred that the vector carry a replication sequence. A preferred vector for use in prokaryotic cells is Bluescript-SK$^+$ (Stratagene). A preferred vector for use in eukaryotic cells is the shuttle vector pEGFP-N (Clontech). This vector encodes a green fluorescent protein (GFP) that has been optimized for maximal activity in mammalian cells and is designed for expression of GFP fusion proteins. This vector also contains a multiple cloning site (MCS) 5' to the GFP sequence which is designed for creating fusion proteins in all three reading frames. The MCS can be used for inserting DNA encoding an RNA of interest to generate a gene encoding a fusion transcript which encodes a fusion protein.

A. Reporter Gene 1

Reporter gene 1 encodes a fusion transcript including, in the 5' portion of the transcript, sequence of an RNA molecule of interest and, in the 3' region of the transcript, sequence encoding the first reporter protein. The sequences are joined so that the fusion transcript encodes a fusion protein that a fusion between the protein encoded by the sequence of the RNA molecule of interest and the reporter protein. This arrangement makes expression of the reporter protein dependent on expression of the RNA of interest. Reporter gene 1 also includes expression sequences necessary for expression of the gene in appropriate host cells.

1. RNA Molecules of Interest

The RNA molecule of interest can be any RNA molecule or portion of an RNA molecule that can be transcribed. It is preferred that the RNA molecule of interest be an RNA molecule involved in the expression of a gene of interest, the expression of which is to be inhibited. The RNA of interest can represent any form of RNA involved in the expression of a gene of interest. For example, the RNA molecule can be a mRNA, a portion of a mRNA, a pre-mRNA including introns, an intron. For introduction into the vector, it is preferred that DNA encoding the RNA molecule of interest be used. A preferred source of DNA encoding RNA molecules of interest are expressed sequence tags (EST). For identification of affector RNA molecules that would inhibit expression at the pre-mRNA stage, intron sequences can be chosen as the RNA molecule of interest.

2. Reporter Protein A

Reporter protein A, also referred to herein as the first reporter protein, can be any protein the expression of which can be detected either directly or indirectly. These include enzymes, such as β-galactosidase, luciferase, and alkaline phosphatase, that can produce specific detectable products, and proteins that can be directly detected. Virtually any protein can be directly detected by using, for example, specific antibodies to the protein. A preferred reporter protein that can be directly detected is the green fluorescent protein (GFP). GFP, from the jellyfish *Aequorea Victoria*, produces fluorescence upon exposure to ultraviolet light without the addition of a substrate (Chalfie et al., *Science* 263:802–5 (1994)). Recently, a number of modified GFPs have been created that generate as much as 50-fold greater fluorescence than does wild type GFP under standard conditions (Cormack et al., *Gene* 173:33–8 (1996); Zolotukhin et al., *J. Virol* 70:4646–54 (1996)). This level of fluorescence allows the detection of low levels of expression in cells.

Reporter proteins producing a fluorescent signal are useful since such a signal allows cells to be sorted using FACS. Another way of sorting cells based on expression of the reporter protein involves using the reporter protein as a hook to bind cells. For example, a cell surface protein such as a receptor protein can be bound by a specific antibody. Cells expressing such a reporter protein can be captured by, for example, using antibodies bound to a solid substrate, using antibodies bound to magnetic beads, or capturing antibodies bound to the reporter protein. Many techniques for the use of antibodies as capture agents are known and can be used with the disclosed method. A preferred form of cell surface protein for use as the first reporter protein is CD8 when the second reporter protein is CD4, otherwise CD4 is preferred.

The first reporter protein can also be a protein that regulates the expression of another gene. This allows detection of expression of the reporter protein by detecting expression of the regulated gene. For example, a repressor protein can be used as the reporter protein. Inhibition of expression of the reporter protein would then result in derepression of the regulated gene. This type of indirect detection allows positive detection of inhibition of the expression of the reporter protein by the affector RNA molecule. One preferred form of this type of regulation is the use of an antibiotic resistance gene regulated by a repressor protein used as the reporter protein. By exposing the host cells to the antibiotic, only those cells in which expression of the reporter gene has been inhibited will grow since expression of the antibiotic resistance gene will be derepressed.

B. Reporter Gene B

Reporter protein B, also referred to herein as the second reporter protein, can be any protein the expression of which can be detected either directly or indirectly. In general, the second reporter protein can be any of the reporter proteins as described above for reporter protein A. The only requirement is that the first and second reporter proteins be different, and that detection of the expression of one not interfere with the detection of expression of the other. It is preferred that the second reporter protein be a protein that confers antibiotic resistance on the host cell or a cell surface protein. The use of an antibiotic resistance protein is preferred in prokaryotic host cells, and the use of a cell surface protein is preferred in eukaryotic host cells. The most preferred cell surface protein for use as the second reporter protein is CD4. The use of a protein conferring antibiotic resistance is not preferred for the first reporter protein since the inhibition of expression is not easily selected.

C. Expression Sequences

The reporter genes can be expressed using any suitable expression sequences. Numerous expression sequences are known and can be used for expression of the reporter genes. Expression sequences can generally be classified as promoters, terminators, and, for use in eukaryotic cells, enhancers. Expression in prokaryotic cells also requires a Shine-Dalgarno sequence just upstream of the coding region for proper translation initiation. Inducible promoters are preferred for use with the first reporter gene since it is preferred that expression of the first reporter gene be adjustable.

Promoters suitable for use with prokaryotic hosts illustratively include the β-lactamase and lactose promoter systems, tetracycline (tet) promoter, alkaline phosphatase promoter, the tryptophan (trp) promoter system and hybrid promoters such as the tac promoter. However, other functional bacterial promoters are suitable. Their nucleotide sequences are generally known.

Suitable promoting sequences for use with yeast hosts include the promoters for 3-phosphoglycerate kinase, enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosphosphate isomerase, phosphoglucose isomerase, and glucokinase. Examples of inducible yeast promoters suitable for use in the disclosed vectors include the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Yeast enhancers also are advantageously used with yeast promoters.

Preferred promoters for use in mammalian host cells include promoters from polymoma virus, Simian Virus 40 (SV40), adenovirus, retroviruses, hepatitis B virus, herpes simplex virus (HSV), Rous sarcoma virus (RSV), mouse mammary tumor virus (MMTV), and most preferably cytomegalovirus (CMV), or from heterologous mammalian promoters such as the β actin promoter. Particularly preferred are the early and late promoters of the SV40 virus and the immediate early promoter of the human cytomegalovirus, MMTV LTR, RSV-LTR, and the HSV thymidine kinase promoter.

Transcription of the reporter gene by higher eukaryotes can be increased by inserting an enhancer sequence into the vector. Many enhancer sequences are now known from mammalian genes (globin, elastase, albumin, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers.

The disclosed vectors preferably also contain sequences necessary for accurate 3' end formation of both reporter and affector RNAs. In eukaryotic cells, this would be a polyadenylation signal. In prokaryotic cells, this would be a transcription terminator.

D. Targeting Gene

The targeting gene encodes and expresses the affector RNA molecule. As used herein, an affector RNA molecule is an RNA molecule that is designed to alter, or preferably inhibit, the expression of an RNA of interest. Preferred affector RNA molecules are ribozymes, external guide sequences, antisense RNA, and triple helix-forming RNA. Ribozymes and external guide sequences inhibit expression of an RNA molecule by cleaving or mediating cleavage of the RNA molecule at a targeted site. Antisense RNA inhibits expression of an RNA molecule through a sequence-specific interaction with the RNA molecule. Triple helix-forming RNA inhibits expression of an RNA molecule by forming a sequence-specific triple helix with DNA encoding the RNA molecule.

1. Affector RNA Molecules

An affector RNA molecule is an RNA molecule that is designed to inhibit the expression of an RNA of interest. Generally, an affector RNA molecule includes a region or regions that mediate the nucleotide base-specific interaction with a targeted sequence in the RNA molecule of interest, or, in the case of triple helix-forming RNA, in DNA encoding the RNA molecule of interest. The region or regions in an affector RNA molecule that mediate the sequence-specific interaction with the targeted sequence in the RNA of interest is referred to herein as the targeting sequence. The term targeting sequence refers collectively to all of the sequences in the affector RNA molecule that together mediate sequence specific interaction. For example, in some ribozymes and eukaryotic external guide sequences, there are two regions that together mediate the required sequence-specific interaction of the ribozyme or EGS with the target RNA molecule. The sequence in the target RNA molecule that is complementary to the targeting sequence of an affector molecule is referred to herein as the targeted site or targeted sequence.

i. Ribozymes and External Guide Sequences

Ribonucleic acid (RNA) molecules can serve not only as carriers of genetic information, for example, genomic retroviral RNA and messenger RNA (mRNA) molecules and as structures essential for protein synthesis, for example, transfer RNA (tRNA) and ribosomal RNA (rRNA) molecules, but also as enzymes which specifically cleave nucleic acid molecules. Such catalytic RNA molecules are called ribozymes.

The use of catalytic RNA in commercial applications, particularly in therapeutics, is reviewed by Altman, *Proc. Natl. Acad. Sci. USA* 90:10898–10900 (1993); Symons, *Annu. Rev. Biochem.* 61:641–671 (1992); Rossi et al., *Antisense Res. Dev.*, 1:285–288 (1991); and Cech, *Annu. Rev. Biochem.* 59:543–568 (1990). Several classes of catalytic RNAs (ribozymes) have been described, including intron-derived ribozymes (WO 88/04300; see also, Cech, *Annu. Rev. Biochem.*, 59:543–568 (1990)), hairpin ribozymes (U.S. Pat. No. 5,527,895 to Hampel et al.), hammerhead ribozymes (WO 89/05852 and EP 321021 by GeneShears), axehead ribozymes (WO 91/04319 and WO 91/04324 by Innovir), as well as RNAase P.

RNAase P is a ribonucleoprotein having two components, an RNA component and a protein component. RNAase P is responsible for the cleavage which forms the mature 5' ends of all transfer RNAs. The RNA component of RNAase P is catalytic. RNAase P is endogenous to all living cells examined to date. During the studies on recognition of substrate by RNAase P, it was found that *E. coli* RNAase P can cleave synthetic tRNA-related substrates that lack certain domains, specifically, the D, T and anticodon stems and loops, of the normal tRNA structure. A half-turn of an RNA helix and a 3' proximal CCA sequence contain sufficient recognition elements to allow the reaction to proceed. The 5' proximal sequence of the RNA helix does not have to be covalently linked to 3' proximal sequence of the helix. The 3' proximal sequence of the stem can be regarded as a "guide sequence" because it identifies the site of cleavage in the 5' proximal region through a base-paired region.

Using these principles, any RNA sequence can be converted into a substrate for bacterial RNAase P by using an external guide sequence, having at its 5' terminus nucleotides complementary to the nucleotides 3' to the cleavage site in the RNA to be cleaved and at its 5' terminus the nucleotides NCCA (N is any nucleotide). This is described in U.S. Pat. No. 5,168,053, WO 92103566 and Forster and Altman, *Science* 238:407409 (1990).

EGS for promoting RNAase P-mediated cleavage of RNA has also been developed for use in eukaryotic systems as described by U.S. Pat. No. 5,624,824, Yuan et al., *Proc. Natl. Acad. Sci. USA* 89:8006–8010 (1992), WO 93/22434, WO 95/24489, WO 96/21731, and in U.S. application Ser. No. 08/615,961, filed Mar. 14, 1996. As used herein, "external guide sequence" and "EGS" refer to any oligonucleotide or oligonucleotide analog that forms, in combination with a target RNA, a substrate for RNAase P. EGS technology has been used successfully to decrease levels of gene expression in both bacteria (Altman et al. (1993)) and mammalian cells in tissue culture (Yuan et al., *Proc. Natl. Acad. Sci. USA* 89:8006–8010 (1992); Liu and Altman, *Genes Dev.* 9:471–480 (1995)).

The ability of EGS molecules to target and promote RNAase P activity is readily determined using an in vitro activity assay for cleavage by RNAase P of a target RNA sequence. In the case of EGS molecules with modified nucleotides or nucleotide linkages, a stability assay allows determination of the nuclease resistance of various types of modification. The activity assay permits comparison of the efficiency of RNAase P-mediated cleavage promoted by EGS molecules with different modifications. Together, the assays can be used to optimize and balance stability and cleavage efficiency of modified EGS molecules.

EGSs and ribozymes having enhanced binding affinity as measured by decreased energy of binding can be designed by in vitro evolution. Such a method can be used to identify RNA molecules with desired properties from pools of molecules that contain randomized sequences. This selection scheme is described in PCT application WO 95/24489 by Yale University. In each round of selection, the pool of RNAs is digested with human RNAase P, or with the ribozyme, and the cleaved products are isolated by electrophoresis and then amplified to produce progeny RNAs. One of the template-creating oligonucleotides is used as the 5' primer for the polymerase chain reaction (PCR) in order to allow restoration of the promoter sequence and the leader sequence of the chimeric RNA for the next cycle of selection. The stringency of selection is increased at each cycle by reducing the amount of enzyme and the time allowed for the cleavage reaction, such that only those substrates that are cleaved rapidly by the enzyme are selected.

a. Prokaryotic External Guide Sequences

The requirements for a EGS functional with prokaryotic RNAase P are less stringent than those for a eukaryotic EGS. The critical elements of a prokaryotic EGS are (1) nucleotide sequence which specifically binds to the targeted RNA substrate to produce a short sequence of base pairs 3' to the cleavage site on the substrate RNA and (2) a terminal 3'-NCCA, where N is any nucleotide, preferably a purine. The sequence generally has no fewer than four, and more usually six to fifteen, nucleotides complementary to the targeted RNA. It is not critical that all nucleotides be complementary, although the efficiency of the reaction will vary with the degree of complementarity. The rate of cleavage is dependent on the RNAase P, the secondary structure of the hybrid substrate, which includes the targeted RNA and the presence of the 3'-NCCA in the hybrid substrate. Eukaryotic external guide sequences, preferred examples of which are described below, also promote cleavage by prokaryotic RNAase P and can be used for this purpose.

b. Eukaryotic External Guide Sequences.

An external guide sequence for promoting cleavage by eukaryotic RNAase P, referred to herein as a eukaryotic EGS, contains sequences which are complementary to the target RNA and which forms secondary and tertiary structure akin to portions of a tRNA molecule. A preferred form of eukaryotic EGS contains at least seven nucleotides which base pair with the target sequence 3' to the intended cleavage site to form a structure like the amino acyl acceptor stem (A stem), nucleotides which base pair to form a stem and loop structure similar to the T stem and loop, followed by at least three nucleotides that base pair with the target sequence to form a structure like the dihydroxyuracil stem. Another preferred form of eukaryotic EGS, referred to herein as a Short External Guide Sequence (SEGS), provide a minimal structure recognized as a substrate by RNAase P when hybridized to a target molecule. The SEGS/target RNA complex includes structures similar to the A stem and the T stem of a tRNA, the natural substrate of RNAase P.

c. Ribozymes

Ribozymes for use in the disclosed method include any trans-cleaving catalytic nucleic acid. Several classes of such ribozymes are known and have been either adapted or designed to cleave RNA molecules in a site-specific manner. In general, ribozymes having such endoribonuclease activity have been derived from self-cleaving RNA molecules by eliminating the site of cleavage from the self-cleaving RNA molecule and re-targeting cleavage to a target RNA molecule by modifying nucleotides in the self-cleaving RNA molecule to interact with the sequence of the target RNA molecule rather than the sequence of the eliminated cleavage site. The region of a ribozyme that interacts with the site of cleavage is referred to as a "guide sequence". For self-cleaving RNA molecules, and ribozymes derived from them, this guide sequence is part of the ribozyme molecule. Such guide sequences are referred to as "internal guide sequences" since they are internal to (that is, part of) the ribozyme. This is in contrast to external guide sequences which are not part of ribozyme molecules.

Intron-derived ribozymes are derived from self-excising introns found in Tetrahymena RNA. Design of ribozymes derived from Tetrahymena introns for the specific cleavage of target RNA molecules and their use is described in U.S. Pat. No. 4,987,071, WO 88/04300, and Cech, *Annu. Rev. Biochem.* 59:543–568 (1990). Hammerhead ribozymes are derived from self-cleaving RNA molecules present in certain viruses. The cleavage activity resides in a region of conserved secondary structure which resembles the head of a hammer (Buzayan et al., *Proc. Natl. Acad. Sci. USA* 83:8859–8862 (1968); Forster and Symons, *Cell* 50:9–16 (1987)). Design of hammerhead ribozymes for the specific cleavage of target RNA molecules and their use is described in U.S. Pat. No. 5,254,678, WO 89/05852, EP 321021, and U.S. Pat. No. 5,334,711. Derivatives of hammerhead ribozymes are described in U.S. Pat. No. 5,334,711; WO 94/13789; and WO 97/18312. Such derivatives, especially those containing chemically modified nucleotides, are particularly preferred for use in the disclosed compositions. Axehead ribozymes are derived from self-cleaving domains in some viroid RNAs. These domains are involved in cleavage of tandemly repeated viroid genomes generated during viroid replication. Design of hairpin ribozymes is described in U.S. Pat. No. 5,527,895 to Hampel et al. Design of axehead ribozymes for the specific cleavage of target RNA molecules and their use is described in U.S. Pat. No. 5,225,337, WO 91/04319, and WO 91/04324. Ribozymes for use in the disclosed method can also be produced using in vitro evolution techniques. Such techniques are described in WO 95/24489 and U.S. Pat. No. 5,580,967.

ii. Triple Helix-forming RNA

Principles and techniques for the design and use of triple helix-forming oligonucleotides are well known. Oligonucleotides are thought to bind as third strands of DNA in a sequence specific manner in the major groove in polypurine/polypyrimidine stretches in duplex DNA. In one motif, a polypyrimidine oligonucleotide binds in a direction parallel to the purine strand in the duplex, as described by Moser and Dervan, *Science* 238:645 (1987), Praseuth et al., *Proc. Natl. Acad. Sci. USA* 85:1349 (1988), and Mergny et al., *Biochemistry* 30:9791 (1991). In the alternate purine motif, a polypurine strand binds anti-parallel to the purine strand, as described by Beal and Dervan, *Science* 251:1360 (1991). The specificity of triplex formation arises from base triplets (AAT and GGC in the purine motif) formed by hydrogen bonding; mismatches destabilize the triple helix, as described by Mergny et al., *Biochemistry* 30:9791 (1991) and Beal and Dervan, *Nuc. Acids Res.* 11:2773 (1992).

Preferably, a triple helix-forming RNA for use as an affector RNA molecule in the disclosed method is between 7 and 40 nucleotides in length, most preferably 20 to 30 nucleotides in length. The base composition is preferably homopurine or homopyrimidine. Alternatively, the base composition is polypurine or polypyrimidine. However, other compositions are also useful. Triple helix-forming RNA should have a base composition which is conducive to triple-helix formation. The sequence of triple helix-forming RNA molecules are preferably designed based on one of the known structural motifs for third strand binding. In the motif used in the Example which follows (the anti-parallel purine motif), a G is used when there is a GC pair and an A is used when there is a AT pair in the target sequence. When there is an inversion, a CG or TA pair, another residue is used, for example, a T is used for a TA pair. A review of base compositions for third strand binding oligonucleotides is provided in U.S. Pat. No. 5,422,251.

Triplex forming oligonucleotides have been found useful for several molecular biology techniques. For example, triplex forming oligonucleotides designed to bind to sites in gene promoters have been used to block DNA binding proteins and to block transcription both in vitro and in vivo. (Maher et al., *Science* 245:725 (1989), Orson et al., *Nucleic Acids Res.* 19:3435 (1991), Postal et al., *Proc. Natl. Acad. Sci. USA* 88:8227 (1991), Cooney et al., *Science* 241:456 (1988), Young et al., *Proc. Natl. Acad. Sci. USA* 88:10023 (1991), Maher et al., *Biochemistry* 31:70 (1992), Duval-Valentin et al., Proc. Natl. Acad. Sci. USA 89:504 (1992), Blume et al., *Nucleic Acids Res.* 20:1777 (1992), Durland et al., *Biochemistry* 30:9246 (1991), Grigoriev et al., *J. of Biological Chem.* 267:3389 (1992), and Takasugi et al., *Proc. Natl. Acad. Sci. USA* 88:5602 (1991)). Site specific cleavage of DNA has been achieved by using triplex forming oligonucleotides linked to reactive moieties such as EDTA-Fe(II) or by using triplex forming oligonucleotides in conjunction with DNA modifying enzymes (Perrouault et al., *Nature* 344:358 (1990), Francois et al., *Proc. Natl. Acad. Sci. USA* 86:9702 (1989), Lin et al., *Biochemistry* 28:1054 (1989), Pei et al., *Proc. Natl. Acad. Sci. USA* 87:9858

(1990), Strobel et al., *Science* 254:1639 (1991), and Posvic and Dervan, *J. Am. Chem Soc.* 112:9428 (1992)). Sequence specific DNA purification using triplex affinity capture has also been demonstrated. (Ito et al., *Proc. Natl. Acad. Sci. USA* 89:495 (1992)). Triplex forming oligonucleotides linked to intercalating agents such as acridine, or to cross-linking agents, such as p-azidophenacyl and psoralen, have been utilized, but only to enhance the stability of triplex binding. (Praseuth et al., *Proc. Natl. Acad. Sci. USA* 85:1349 (1988), Grigoriev et al., *J. of Biological Chem.* 267:3389 (1992), Takasugi et al., *Proc. Natl. Acad. Sci. USA* 88:5602 (1991). Triple helix-forming oligonucleotides for mutagenesis are described in WO 96/40898.

2. Self-cleaving Ribozymes

A self-cleaving ribozyme can also be included downstream of the region encoding the affector RNA molecule. Such a ribozyme is used to cleave the targeting gene transcript to produce an affector RNA molecule with a defined 3' end. This self-cleaving ribozyme is in addition to the affector RNA molecule and should not be confused with a trans-cleaving ribozyme used as the affector RNA molecule. A self-cleaving ribozyme can also be included upstream of the affector RNA molecule. Preferred self-cleaving ribozymes for cleaving the targeting gene transcript are hammerhead ribozymes. Self-cleaving ribozymes for use in the targeting gene can generally be designed using the same principles used for the design of trans-cleaving ribozymes as described above. The only difference is the inclusion of the substrate sequence in the ribozyme.

3. Expression Sequences

The targeting gene includes expression sequences for the expression of the affector RNA molecule. It is preferred that the promoter used in the targeting gene is a promoter from a gene encoding a non-translated RNA, such as a ribosomal RNA gene promoter, a transfer RNA gene promoter, or a promoter from a gene encoding the RNA component of a ribonucleoprotein. Preferred promoters for use in prokaryotes include the M1 promoter, ribosomal promoters, the f1 phage gene 5 promoter, and the T7 promoter. Use of the T7 promoter requires the expression of the T7 RNA polymerase in the host cell.

Preferred promoters for expressing the targeting gene in eukaryotic cells are either RNA polymerase III (pol III) promoters lacking internal elements or RNA polymerase II (pol II) promoters characteristic of small nuclear RNA (snRNA) genes (for example, U1, U2, and U4). Such promoters can produce transcripts constitutively without cell type specific expression. These promoters also generate transcripts that can be engineered to remain in the nucleus of the cell, the location of many target RNA molecules. It is preferred that a complete transcription unit be used, including a promoter and a termination sequence. Preferred pol III promoters for use in EGS expression vectors are the human small nuclear U6 gene promoter and the promoter for human RNAse P RNA. The use of U6 gene transcription signals to produce short RNA molecules in vivo is described by Noonberg et al., *Nucleic Acids Res.* 22:2830–2836 (1995), and the use of RNAse P promoters is described by Baer et al., *Nucleic Acids Res.* 18:97–103 (1990) and Hannon et al., *J. Biol. Chem.* 266:22796–22799 (1991). The use of snRNA pol II promoters is described by Zhuang and Weiner, *Cell* 46:827–835 (1986).

The U6 gene promoter is not internal (Kunkel and Pederson, *Nucleic Acids Res.* 18:7371–7379 (1989); Kunkel et al., *Proc. Natl. Acad. Sci. USA* 83:8575–8579 (1987); Reddy et al., *J. Biol. Chem.* 262:75–81 (1987)). Suitable pol III promoter systems useful for expression of EGS molecules are described by Hall et al., *Cell* 29:3–5 (1982), Nielsen et al., *Nucleic Acids Res.* 21:3631–3636 (1993), Fowlkes and Shenk, *Cell* 22:405413 (1980), Gupta and Reddy, *Nucleic Acids Res.* 19:2073–2075 (1990), Kickoefer et al., *J. Biol. Chem.* 268:7868–7873 (1993), and Romero and Blackburn, *Cell* 67:343–353 (1991). The use of pol III promoters for expression of ribozymes is also described in WO 95/23225 by Ribozyme Pharmaceuticals, Inc.

The targeting gene should also include a transcription terminator, a self-cleaving ribozyme, or both, downstream from the region encoding the affector RNA molecule. The affector molecule may function more effectively if it does not include extraneous 3' sequences. A transcription terminator prevents transcription from continuing into the vector. To be effective, the transcription terminator should be functional with the type of RNA polymerase used to transcribe the targeting gene.

E. Replication Sequences

The disclosed vectors can be used to transiently transfect or transform host cells, or can be integrated into the host cell chromosome. Preferably, however, the vectors can include sequences that allow replication of the vector and stable or semi-stable maintenance of the vector in the host cell. Many such sequences for use in various cells (that is, eukaryotic and prokaryotic cells) are known and their use in vectors routine. Generally, it is preferred that replication sequences known to function in host cells of interest be used. For example, use of the origin of replication from vectors such as pBR322 and pUC19 are preferred for prokaryotic cells, origins of replication from such vectors as YEP24 and YRP17 are preferred for fungal cells, and origins of replication from SV40 and pEGFP-N. All of these examples are readily available (New England Biolabs; Clontech).

II. Affector Oligomers

Functional or efficient affector molecules identified using the disclosed method can be used to design oligomers that are based on the affector RNA molecule or are targeted to the same site as the selected affector RNA molecule. The affector molecules selected using the disclosed method and the targeting sequences present in these affector molecules provide information that can be used to design affector nucleic acids or oligomers that have the same nucleotide base sequence as the selected affector molecule, have the same targeting sequence as the selected affector RNA molecule, or are targeted to the same site or region of the RNA molecule of interest as the selected affector RNA molecule.

General principles of the design of ribozymes, external guide sequences, antisense oligomers, and triple helix-forming oligomers are known and can be used to design affector oligomers. The disclosed method provides useful information about accessible target sites in an RNA of interest and about targeting sequences that are effective for targeting an affector RNA molecule to an RNA of interest. This target site and targeting sequence information is directly and easily applied to the design of targeting sequences in any type of affector molecule. For example, the targeting sequence of a functional EGS identified using the disclosed method can be used directly as the targeting sequence of any other EGS of whatever form, and can be adapted for use as the targeting sequence of a ribozyme, antisense molecule, or triple helix-forming molecule. The principles of the design of targeting sequences in ribozymes, external guide sequences, antisense molecules, and triple helix-forming molecules are well known and are generally adaptable to any or most target sites identified in an RNA molecule of interest. By identifying accessible sites in RNA molecules of interest, the disclosed method provides useful information for the design of affector molecules.

As used herein, an affector oligomer is an oligomeric molecule that is designed to inhibit the expression of an RNA of interest. Preferred affector oligomers are ribozymes, external guide sequences, antisense RNA, and triple helix-forming RNA. As used herein, oligomer refers to oligomeric molecules composed of subunits where the subunits can be of the same class (such as nucleotides) or a mixture of classes. It is preferred that the disclosed oligomers be oligomeric sequences. It is more preferred that the disclosed oligomers be oligomeric sequences. Oligomeric sequences are oligomeric molecules where each of the subunits includes a nucleobase (that is, the base portion of a nucleotide or nucleotide analogue) which can interact with other oligomeric sequences in a base-specific manner. The hybridization of nucleic acid strands is a preferred example of such base-specific interactions. Oligomeric sequences preferably are comprised of nucleotides, nucleotide analogues, or both, or are oligonucleotide analogues.

As used herein, nucleoside refers to adenosine, guanosine, cytidine, uridine, 2'-deoxyadenosine, 2'-deoxyguanosine, 2'-deoxycytidine, or thymidine. A nucleoside analogue is a chemically modified form of nucleoside containing a chemical modification at any position on the base or sugar portion of the nucleoside. As used herein, the term nucleoside analogue encompasses, for example, both nucleoside analogues based on naturally occurring modified nucleosides, such as inosine and pseudouridine, and nucleoside analogues having other modifications, such as modifications at the 2' position of the sugar. As used herein, nucleotide refers to a phosphate derivative of nucleosides as described above, and a nucleotide analogue is a phosphate derivative of nucleoside analogues as described above. The subunits of oligonucleotide analogues, such as peptide nucleic acids, are also considered to be nucleotide analogues.

As used herein, a ribonucleotide is a nucleotide having a 2' hydroxyl function. Analogously, a 2'-deoxyribonucleotide is a nucleotide having only 2' hydrogens. Thus, ribonucleotides and deoxyribonucleotides as used herein refer to naturally occurring nucleotides having nucleoside components adenosine, guanosine, cytidine, and uridine, or 2'-deoxyadenosine, 2'-deoxyguanosine, 2'-deoxycytidine, and thymidine, respectively, without any chemical modification. Ribonucleosides, deoxyribonucleosides, ribonucleoside analogues and deoxyribonucleoside analogues are similarly defined except that they lack the phosphate group, or an analogue of the phosphate group, found in nucleotides and nucleotide analogues.

As used herein, oligonucleotide analogues are polymers of nucleic acid-like material with nucleic acid-like properties, such as sequence dependent hybridization, that contain at one or more positions, a modification away from a standard RNA or DNA nucleotide. A preferred example of an oligonucleotide analogue is peptide nucleic acid.

As used herein, base pair refers to a pair of nucleotides or nucleotide analogues which interact through one or more hydrogen bonds. The term base pair is not limited to interactions generally characterized as Watson-Crick base pairs, but includes non-canonical or sheared base pair interactions (Topal and Fresco, *Nature* 263:285 (1976); Lomant and Fresco, *Prog. Nucl. Acid Res. Mol. Biol.* 15:185 (1975)).

The internucleosidic linkage between two nucleosides can be achieved by phosphodiester bonds or by modified phospho bonds such as by phosphorothioate groups or other bonds such as, for example, those described in U.S. Pat. No. 5,334,711.

III. Method

The disclosed method identifies functional affector RNA molecules, such as ribozymes, external guide sequences, antisense RNA, and triple helix-forming RNA, by screening or selecting for those affector RNA molecules that alters expression of a transcript that is a fusion of an RNA molecule of interest and RNA encoding a reporter protein. In the preferred embodiments, expression is inhibited. As used herein, inhibition refers to a decrease in expression and not necessarily an elimination of expression. Inhibition of expression of the fusion transcript prevents or decreases expression of the reporter protein. This allows inhibition to be monitored by detecting expression of the reporter protein. The disclosed method can be performed using either prokaryotic or eukaryotic cells.

The method is generally performed by constructing a set of vectors that are the same except that each vector encodes a different affector RNA molecule. Each of the affector RNA molecules are targeted to a different site in the RNA of interest. Alternatively, the targeting sequence in the affector RNA molecules can be made fully or partially degenerate such that the set includes targeting sequences specific for a variety of possible target sequences. The set of vectors can then introduced into appropriate host cells and the cells can then be screened or selected for expression of reporter gene 2. These cells are then screened for inhibition of expression of reporter protein 1. If appropriate, expression of both the first and second reporter genes can be assessed simultaneously. The vectors in the selected cells are then identified. This can be accomplished by, for example, probing the cells or DNA from the cells for the presence of specific sequences, or sequencing a specific portion of the vectors. Vectors can also be isolated from the selected cells and re-introduced into host cells. Screening can be repeated and the affector RNA molecules present on the vectors can be identified, preferably by nucleic acid sequence analysis.

A. Construction of Vectors

The disclosed vectors, the components of which are described above, can be constructed using well established recombinant DNA techniques (see, for example, Sambrook et al., Molecular Cloning: A Laboratory Manual, second edition, Cold Spring Harbor Laboratory Press, New York (1990)). It is preferred that a base vector be prepared first. Then DNA encoding an RNA molecule of interest can be inserted into this base vector to form a second base vector. A different second base vector can be constructed for each RNA molecule of interest. Finally, libraries of DNA encoding affector RNA molecules can be inserted into appropriate second base vectors. The same base vector can be easily used with any RNA molecule of interest, and the same second base vector can be used with any appropriate library of affector RNA molecules. For example, the same second base vector can be used for a library of ribozymes, a library of external guide sequences, a library of antisense RNA molecules, and a library of triple helix-forming RNA molecules.

B. Introduction of Vectors into Cells

Host cells can be transformed with the disclosed vectors using any suitable means and cultured in conventional nutrient media modified as is appropriate for inducing promoters, selecting transformants or detecting expression. Suitable culture conditions for host cells, such as temperature and pH, are well known. The concentration of plasmid used for cellular transfection is preferably titrated to reduce the possibility of expression in the same cell of multiple vectors encoding different affector RNA molecules.

Preferred prokaryotic host cells for use in the disclosed method are *E. coli* cells. Preferred eukaryotic host cells for use in the disclosed method are monkey kidney CVI line transformed by SV40 (COS-7, ATCC CRL 1651); human embryonic kidney line (293, Graham et al. J. Gen Virol. 36:59 [1977]); baby hamster kidney cells (BHK, ATCC CCL 10); chinese hamster ovary-cells-DHFR (CHO, Urlaub and Chasin, Proc. Natl. Acad. Sci. (USA) 77:4216, [1980]); mouse sertoli cells (TM4, Mather, Biol. Reprod. 23:243–251 [1980]); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL51); TRI cells (Mather et al., Annals N. Y. Acad. Sci 383:44–68 (1982)); human B cells (Daudi, ATCC CCL 213); human T cells (MOLT-4, ATCC CRL 1582); and human macrophage cells (U-937, ATCC CRL 1593).

C. Screening for or Selection of Reporter Gene 2 Expression

Cells expressing the second reporter gene are identified by detecting the presence of reporter protein B either directly or indirectly. Reporter gene 2 is used to insure that the cells contain the vector and to control for any factors that could affect expression in general. Without such a control, a loss of expression of reporter gene 1 could be misinterpreted. For this purpose, it is not important that the level of expression of reporter gene 2 be measured. It is preferred that reporter protein B is an essential protein for the cell, such as a protein that confers antibiotic resistance or a protein that produces a required nutrient not present in culture medium. In this way, cells expressing reporter gene 2 can be easily selected by using appropriate cell culture conditions. For eukaryotic cells, it is preferred that reporter protein B is a cell surface protein. Such a protein, exposed on the surface of cells expressing reporter gene 2, can be used to effectively sort the cells. There are many ways that such sorting can be accomplished, many of which have been developed for sorting cells that naturally express a particular cell surface protein. For example, many cell sorting techniques are known for CD4 and CD8. A cell surface protein can be bound by an antibody specific for the protein. If the antibody is labeled, labeled cells can be separated from unlabeled cells using, for example, FACS. The antibody can also be coupled to a solid support or to beads. Cells expressing the cell surface protein can then be retained on the solid support or separated using the attached beads. For this purpose, magnetic beads are preferred.

It is preferred that peridinin chlorophyll-conjugated antibody (PerCP) be used for cells expressing CD8 as the second reporter protein when the first reporter protein is GFP since PerCP fluoresces at a wavelength that does not overlap with GFP fluorescence. PerCP-conjugated CD8 antibody is available from Becton Dickinson.

D. Screening for or Selection of Lack of Reporter Protein 1 Expression

Cells in which expression of the first reporter gene is altered can be identified by measuring the level of expression of reporter protein A either directly or indirectly, or by separating cells based on the expression level of reporter protein A. The preferred method of detection will depend on the nature of reporter protein being used. For example, when using a reporter protein that produces a detectable signal proportionate to the level of expression, cells can be sorted or picked based on the level of signal produced. Reporter proteins such as β-galactosidase and green fluorescent protein are in this category. When using a cell surface protein as reporter protein A, the cell sorting techniques described above can be used. Cells can also be sorted by FACS when using green fluorescent protein as reporter protein A since it produces a fluorescent signal.

It is preferred that the above selection process can be repeated several times, by isolating vectors from the selected cells and re-introducing them into new cells, until cells bearing a homogeneous population of plasmids can be isolated. Following the final sorting of cells, the vectors can be isolated as described below, amplified, and the sequence of the affector RNA molecule encoded in each preparation of vector can be determined.

E. Identification of Functional Ribozymes or External Guide Sequences

Affector RNA molecules that are effective inhibitors of expression of reporter gene 1 can be identified using any suitable technique. It is preferred that the sequence of the functional affector RNA molecules be determined by sequencing the vectors in the selected cells. Many techniques for sequencing vector sequences from clones are known and can be used in the disclosed method. For example, Hirt supernatants of selected cells can be made and plasmids will be extracted from those cells. A preferred method for identifying the sequence of the affector RNA molecules in the isolated vectors is a single cell PCR amplification of the affector RNA region, followed by sequencing. Another preferred method for identifying the sequence of the affector RNA molecules in the isolated vectors is to lyse the cells, extract the plasmids, amplify the plasmids in bacteria, and sequence the amplified plasmids to identify the affector RNA molecule sequence associated with the cell population.

Functional or efficient affector molecules identified using the disclosed method can be used to design oligomers based on the affector RNA molecule or targeted to the same site as the affector RNA molecule. The design of such affector oligomers is described above.

EXAMPLES

Example 1

Transformation in a Single Plasmid

A set of the vectors encoding a first reporter gene encoding GFP as reporter protein A, a second reporter gene, and targeting gene encoding a library of EGS or ribozyme molecules as the affector RNA molecules are amplified by growing the mixed population in *E. coli*. A fixed concentration of mixture of plasmids is complexed with an appropriate carrier (for example, lipid, calcium phosphate, DEAE dextran) and delivered to mammalian cells. At the peak day of expression (usually day two), the level of expression of GFP and the second reporter are measured by FACS sorting. The expression of the second reporter (for example, CD4) is measured at a wavelength that does not overlap with GFP fluorescence spectrum. Typically, an antibody conjugated with a fluorescent tag is used and directed against the second reporter protein to monitor the level of expression of the second reporter. The antibody is incubated with the cells, excess antibody is washed off, and the fluorescence is monitored at a wavelength different from GFP. The ratio of GFP expression to second reporter expression is used as a measure to determine the degree of inhibition of expression of the target sequence. The cells are lysed, plasmid extracted, amplified in bacteria, and sequenced to identify the EGS/ribozyme associated with the cell population.

Example 2

Transformation in Two Separate Plasmids

In another embodiment, two separate plasmids are used to transform *E. coli*. The first one encodes the fusion protein (target-GFP) and the second one encodes the second reporter and the targeting gene encoding a library of EGS/ribozymes. The plasmids encoding the EGS/ribozyme library are grown in bacteria and mixed plasmids prepared as in Example 1.

A fixed concentration of the mixed plasmids (each encoding a separate EGS or ribozyme) is combined with a fixed concentration of the target plasmid (encoding the target-GFP fusion protein). The mixture is complexed with a commercially available preparation of lipid or calcium phosphate and transfected to cells plated in 96 wells. At the peak of expression of GFP, the levels of GFP-fluorescence and the level of expression of the second reporter are measured and the ratio of GFP expression to second reporter is used to determine the efficacy of EGS or ribozyme. The ratio of EGS to target can be altered to change the level of expression of the EGS/ribozyme over the target.

Example 3

Selecting Functional EGS from a Pool of EGS

A prokaryotic base vector including a fusion protein of CAT-β-galactosidase expressed dark blue colonies. A library of DNA encoding 55 EGS was inserted into the targeting gene of the base vector.

Two libraries were made. The first library, Library A, encoded EGS followed by a T7 terminator. The second library encoded EGS followed by a self-cleaving hammerhead ribozyme to mature 3' end of the EGS. Expression in the second library was lower, presumably due to lower stability.

Library A was plated on X-gal plates. Light and dark blue colonies were counted. Light blue colonies were presumed to show EGS-mediated interference of CAT expression. Colonies grown from the EGS library provided approximately 5% light blue colonies, compared to less than 1% of light blue colonies on control plates (those colonies grown from libraries without EGS insertions). This total number of positives was consistent with two to three EGS sequences out of the original library being effective. Accordingly, a tight grouping of sequences was expected. Therefore, light blue colonies were picked and replated. The light blue color was preserved. Most of the light blue colonies were assayed for β-galactosidase activity and manifested an 80 to 90% inhibition of enzyme activity.

DNA from four of the light blue colonies was isolated and sequenced. Each colony encoded the same EGS. This EGS was inserted into the base vector. Approximately 90% inhibition of CAT activity was observed. Qualitatively, less inhibition was seen with the second library.

As a control, the converse experiment was performed. The EGS was removed from the base vector. Wild type levels of β-galactosidase expression were observed. This data indicates that functional EGS can be selected from a large pool. EGSs 1 and 2, previously identified functional EGS targeted to CAT RNA, show little or no activity in these assays.

Thirty-nine positives from Library A were selected through tertiary screening. DNA was prepared and sequenced. Only eight of the original 53 EGS sequences were found, with EGS number 52 recurring twenty three times. As a control, forty eight colonies were selected from Library A at random without regard to the expression level of β-galactosidase. In this random set, twenty eight EGS sequences were found, no one sequence recurring more than five times. Table 1 shows the distribution of the EGS sequences.

TABLE 1

Distribution of EGS Sequences.

| EGS | No. Found Randoms | No. Found Selected |
|---|---|---|
| 1 | 0 | 0 |
| 2 | 1 | 0 |
| 3 | 1 | 0 |
| 4 | 0 | 0 |
| 5 | 0 | 0 |
| 6 | 0 | 0 |
| 7 | 0 | 0 |
| 8 | 0 | 1 |
| 9 | 1 | 0 |
| 10 | 0 | 0 |
| 11 | 2 | 0 |
| 12 | 3 | 0 |
| 13 | 0 | 3 |
| 14 | 3 | 0 |
| 15 | 0 | 0 |
| 16 | 0 | 0 |
| 17 | 0 | 0 |
| 18 | 2 | 0 |
| 19 | 1 | 0 |
| 20 | 2 | 3 |
| 21 | 5 | 1 |
| 22 | 0 | 0 |
| 23 | 1 | 0 |
| 24 | 1 | 0 |
| 25 | 1 | 0 |
| 26 | 1 | 0 |
| 27 | 0 | 0 |
| 28 | 0 | 0 |
| 29 | 0 | 0 |
| 30 | 0 | 0 |
| 31 | 1 | 3 |
| 32 | 0 | 0 |
| 33 | 1 | 0 |
| 34 | 3 | 0 |
| 35 | 1 | 1 |
| 36 | 1 | 5 |
| 37 | 1 | 0 |
| 38 | 2 | 0 |
| 39 | 0 | 0 |
| 40 | 1 | 0 |
| 41 | 0 | 0 |
| 42 | 0 | 0 |
| 43 | 4 | 0 |
| 44 | 0 | 0 |
| 45 | 2 | 0 |
| 46 | 0 | 0 |
| 47 | 0 | 0 |
| 48 | 1 | 0 |
| 49 | 0 | 0 |
| 50 | 2 | 0 |
| 51 | 0 | 0 |
| 52 | 2 | 23 |
| CAT1 | 1 | 0 |
| CAT2 | 0 | 0 |
| Total | 48 | 39 |

Figure 3A:
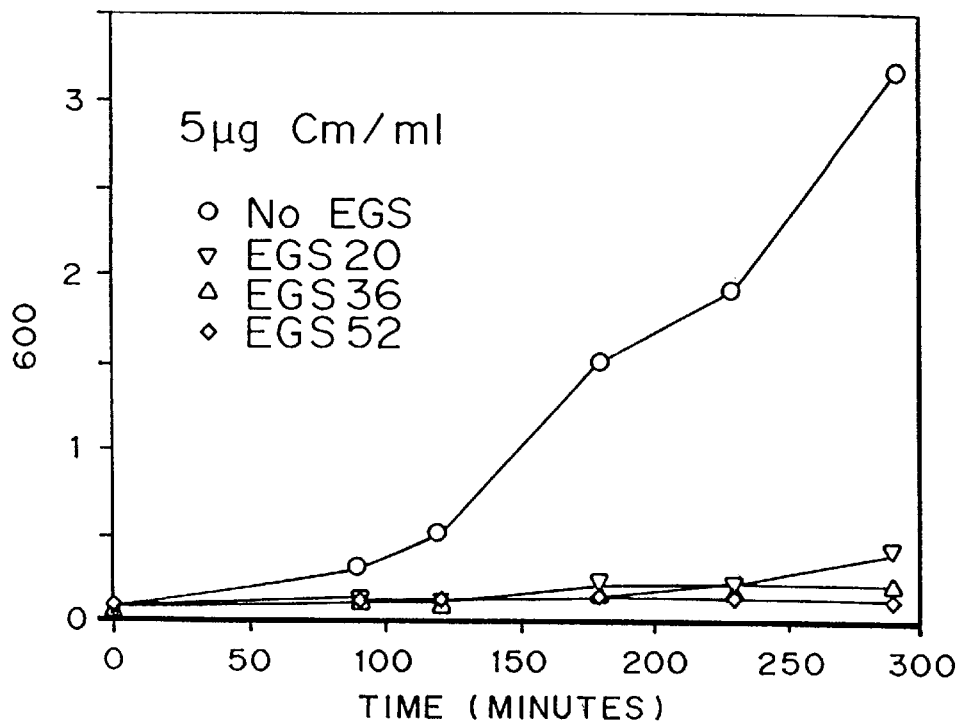
FIGS. 3A–B is graph of cell culture density ($A_{600}$) versus time (in minutes) of cells in the presence of 5 μg/ml chloramphenicol (FIG. 3A) or 25 μg/ml chloramphenicol (FIG. 3B). The cells contained a vector similar to the vector shown in FIG. 2 that did not encode an EGS (circles), encoded EGS 36 (triangles), encoded EGS 20 (inverted triangles), or encoded both EGS 52 (diamonds).
Figure 3B:
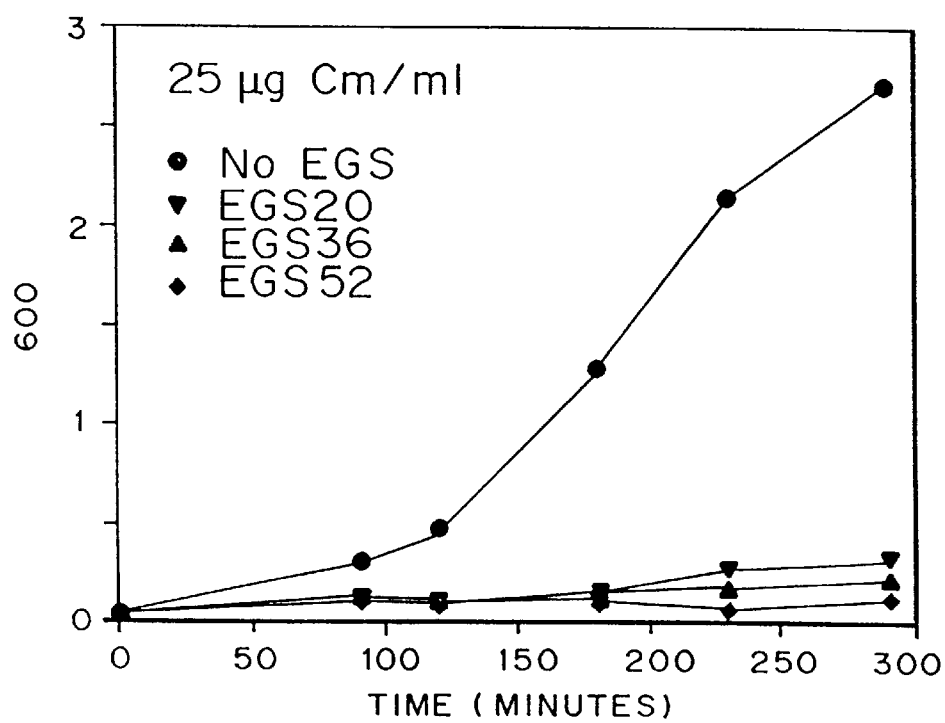

Therefore, by these criteria, EGS 52, EGS 36 and EGS 20 were identified as the most frequently selected EGS molecules. These same EGS molecules should be the most effective at inhibition of CAT gene expression. To test this, EGS 52, EGS 36, and EGS 20 were expressed in cells expressing a CAT gene, and the cells were challenged with chloramphenicol. The results are shown in FIGS. 3A–B. All three of the selected EGS molecules have a significant effect on chloramphenicol resistance, while cells with a control plasmid lacking any EGS exhibit chloramphenicol resistance.

Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A nucleic acid molecule comprising a first reporter gene, a second reporter gene, and a targeting gene, wherein the first reporter gene encodes a fusion protein comprising a protein of interest and a first reporter protein, wherein the second reporter gene encodes a second reporter protein, wherein the protein of interest is encoded by an RNA of interest, wherein the targeting gene encodes an affector RNA molecule, wherein the affector RNA molecule is targeted to a site on the RNA molecule of interest or to a site in the portion of the first reporter gene encoding the RNA molecule of interest.

2. The nucleic acid molecule of claim 1 wherein the affector RNA molecule encoded by the targeting gene is selected from the group consisting of external guide sequences, ribozymes, antisense RNA, and triple helix-forming RNA.

3. The nucleic acid molecule of claim 1 wherein the nucleic acid molecule is a vector.

4. The nucleic acid molecule of claim 3 wherein the vector is functional in prokaryotic cells.

5. The nucleic acid molecule of claim 4 wherein the first reporter protein is detectable or produces a detectable product, the second reporter protein provides antibiotic resistance to a cell harboring the vector.

6. The nucleic acid molecule of claim 5 wherein the first reporter protein is green fluorescent protein or is derived from β-galactosidase.

7. The nucleic acid molecule of claim 3 wherein the vector is functional in eukaryotic cells.

8. The nucleic acid molecule of claim 7 wherein the first reporter protein is detectable or produces a detectable product, the second reporter protein is a cell surface protein.

9. The nucleic acid molecule of claim 8 wherein the first reporter protein is a cell surface protein.

10. The nucleic acid molecule of claim 8 wherein the cell surface protein is CD4.

11. A set of nucleic acid molecules wherein each nucleic acid molecule comprises a first reporter gene, a second reporter gene, and a targeting gene, wherein the first reporter gene encodes a fusion protein comprising a protein of interest and a first reporter protein, wherein the second reporter gene encodes a second reporter protein, wherein the protein of interest is encoded by an RNA of interest, wherein the targeting gene encodes an affector RNA molecule, wherein the affector RNA molecule is targeted to a site on the RNA molecule of interest or to a site in the portion of the first reporter gene encoding the RNA molecule of interest, wherein each nucleic acid molecule in the set is the same except for the encoded affector RNA molecule, wherein the affector RNA molecule encoded in each nucleic acid molecule in the set is targeted to a different site on the RNA molecule of interest or to a different site in the portion of the first reporter gene encoding the RNA molecule of interest.

12. The set of claim 11 wherein the affector RNA molecule encoded by the targeting gene on each of the nucleic acid molecules in the set is selected from the group consisting of external guide sequences, ribozymes, antisense RNA, and triple helix-forming RNA.

13. The set of claim 12 wherein the affector RNA molecule encoded by the targeting gene on each of the nucleic acid molecules in the set is an external guide sequence.

14. The set of claim 12 wherein the affector RNA molecule encoded by the targeting gene on each of the nucleic acid molecules in the set is a ribozyme.

15. The set of claim 12 wherein the affector RNA molecule encoded by the targeting gene on each of the nucleic acid molecules in the set is an antisense RNA.

16. The set of claim 12 wherein the affector RNA molecule encoded by the targeting gene on each of the nucleic acid molecules in the set is a triple helix-forming RNA.

17. A set of nucleic acid molecules wherein each nucleic acid molecule comprises a first reporter gene, a second reporter gene, and a targeting gene, wherein the first reporter gene encodes a fusion protein comprising a protein of interest and a first reporter protein, wherein the second reporter gene encodes a second reporter protein, wherein the protein of interest is encoded by an RNA of interest, wherein the targeting gene encodes an affector RNA molecule comprising a targeting sequence, wherein each nucleic acid molecule in the set is the same except for the encoded affector RNA molecule, wherein the targeting sequence of the affector RNA molecule in each nucleic acid molecule is overlapping or partially overlapping.

18. The set of claim 17 wherein the affector RNA molecules encoded by the nucleic acid molecules in the set are collectively targeted to every possible sequence having the same length as the targeting sequence of the affector RNA molecules.

19. A set of nucleic acid molecules wherein each nucleic acid molecule comprises a reporter gene and a targeting gene, wherein the reporter gene encodes a fusion protein comprising a protein of interest and a reporter protein, wherein the protein of interest is encoded by an RNA of interest, wherein the targeting gene encodes an affector RNA molecule, wherein each nucleic acid molecule in the set is the same except for the encoded affector RNA molecule, wherein the affector RNA molecule encoded by each nucleic acid molecule is targeted to a different site on the RNA molecule of interest or to a different site in the portion of the first reporter gene encoding the RNA molecule of interest.

20. The set of claim 19 wherein the set comprises more than five nucleic acid molecules.

21. The set of claim 20 wherein the set comprises more than twenty nucleic acid molecules.

22. A method of identifying affector RNA molecules that reduce the expression of an RNA of interest, the method comprising (a) introducing into cells a set of nucleic acid molecules wherein, after introduction of the nucleic acid molecules, each cell comprises a first reporter gene, a second reporter gene, and a targeting gene, wherein the first reporter gene encodes a fusion protein comprising a protein of interest and a first reporter protein, wherein the second reporter gene encodes a second reporter protein, wherein the protein of interest is encoded by an RNA of interest, wherein the targeting gene encodes an affector RNA molecule comprising a targeting sequence, wherein each nucleic acid molecule in the set is the same except for the encoded affector RNA molecule, wherein (1) the affector RNA molecule encoded in each nucleic acid molecule in the set is targeted to a different site on the RNA molecule of interest or to a different site in the portion of the first reporter gene encoding the RNA molecule of interest, or (2) the targeting sequence of the affector RNA molecule in each nucleic acid molecule is degenerate or partially degenerate, (b) identifying those cells from step (a) that both express the second reporter protein and exhibit reduced expression of the first reporter protein, and (c) identifying the affector RNA molecules encoded by the nucleic acid molecules present in the cells that both express the second reporter protein and exhibit reduced expression of the first reporter protein,
wherein the affector RNA molecules identified are affector RNA molecules that reduce the expression of an RNA of interest.

23. The method of claim 22 wherein cells that both express the second reporter protein and exhibit reduced expression of the first reporter protein are identified by
screening the cells from step (a) for, or selecting from the cells from step (a), cells that express the second reporter protein, and
screening the cells that express the second reporter protein, or selecting from the cells that express the second reporter protein, cells that exhibit reduced expression of the first reporter protein.

24. The method of claim 23 wherein screening for cells that express the second reporter protein is accomplished by FACS.

25. The method of claim 23 wherein selecting for cells that express the second reporter protein is accomplished by antibiotic selection.

26. The method of claim 23 wherein screening for cells that express the second reporter protein is accomplished by antibody-mediated sorting or ligand-mediated sorting.

27. The method of claim 23 wherein screening for cells that exhibit reduced expression of the first reporter protein is accomplished by FACS.

28. The method of claim 22 wherein affector RNA molecules encoded by the nucleic acid molecules present in the cells that both express the second reporter protein and exhibit reduced expression of the first reporter protein are identified by identifying the nucleic acid molecules present in the cells that both express the second reporter protein and exhibit reduced expression of the first reporter protein.

29. The method of claim 28 wherein the nucleic acid molecules present in the cells that both express the second reporter protein and exhibit reduced expression of the first reporter protein are identified by
isolating the nucleic acid molecules present in the cells that both express the second reporter protein and exhibit reduced expression of the first reporter protein, and determining the sequence of the portion of the targeting gene encoding the targeting sequence, or
determining the sequence of the portion of the targeting gene encoding the targeting sequence by nucleic acid hybridization.

30. The method of claim 22 wherein the expression of the first reporter protein exhibited by cells selected or screened for in step (c) is reduced relative to cells containing a control nucleic acid molecule that does not express a functional affector RNA molecule.

31. The method of claim 22 wherein the first reporter gene, the second reporter gene, and the targeting gene are all present on each nucleic acid molecule.

32. The nucleic acid molecule of claim 1 wherein the affector RNA molecule encoded by the targeting gene is an external guide sequence.

33. The method of claim 22 wherein the affector RNA molecule encoded by the targeting gene is an external guide sequence.

34. The set of claim 11 wherein the affector RNA molecules encoded by the nucleic acid molecules in the set are collectively targeted to every possible sequence having the same length as the targeting sequence of the affector RNA molecules.

* * * * *